US00PP09153P

United States Patent [19]

Wyckoff

[11] Patent Number: Plant 9,153

[45] Date of Patent: Jun. 6, 1995

[54] HYBRID TEA ROSE PLANT NAMED 'HAWAIIAN KING'

[76] Inventor: Gilbert R. Wyckoff, HCR 2, Box 6026, Keaau, Hi. 96749

[21] Appl. No.: 194,163

[22] Filed: Apr. 4, 1994

[51] Int. Cl.[6] ..... A01H 5/00

[52] U.S. Cl. ..... Plt./18

[58] Field of Search ..... Plt. 18, 11

[56] References Cited

U.S. PATENT DOCUMENTS

P.P. 5,165 12/1983 Kriloff ..... Plt./18
P.P. 6,031 10/1987 Marciel ..... Plt./18
P.P. 7,739 12/1991 Suzuki ..... Plt./18

*Primary Examiner*—Howard J. Locker

[57] ABSTRACT

A hybrid tea class rose plant with many fine attributes for the home gardner or the exhibitionist: unusual light pink and deep pink petal coloration, long lasting on bush or as a cut flower; 22 to 26 inch cutting stems and pleasant, moderately strong sweet fragrance.

2 Drawing Sheets

This present invention relates to a new and distinct variety of rose plant of the hybrid tea class which was originated by me by crossing the variety Peggy Lee (seed parent) with the variety Captain Harry Stebbings (pollen parent). Peggy Lee is a light pink sport of the HT rose Century Two (medium pink) and Captain Harry Stebbings is a deep pink HT rose with a high exhibition rating.

The primary objective of this breeding was to produce a new rose variety which had an unusual and distinctive pink color combination, along with good foliage and long stems. As both parent roses had much color variations in their breeding, I felt that this cross could produce favorable results. My objective was substantially achieved as evidenced by the following unique combination of characteristics which distinguish it from its parents as well as from all other varieties of which I am aware, and making it an excellent garden and exhibition type rose:

1. Long cutting stems, 22 to 26 inches.
2. Unusual pink petal coloration.
3. Moderately strong sweet fragrance.
4. 55 to 60 petals with much substance; long-lasting on bush or as a cut flower.

Asexual reproduction by budding and rooted cuttings, performed in the Hilo, Hawaii area, shows that all characteristics and distinctions come true to form and are transmitted through succeeding propagations.

The accompanying photographic illustrations show typical specimens of the vegetative growth and flowers of this new variety in different stages of development, depicted in color as nearly true as it is reasonably possible to attain in color illustrations of this character.

Figure 1:
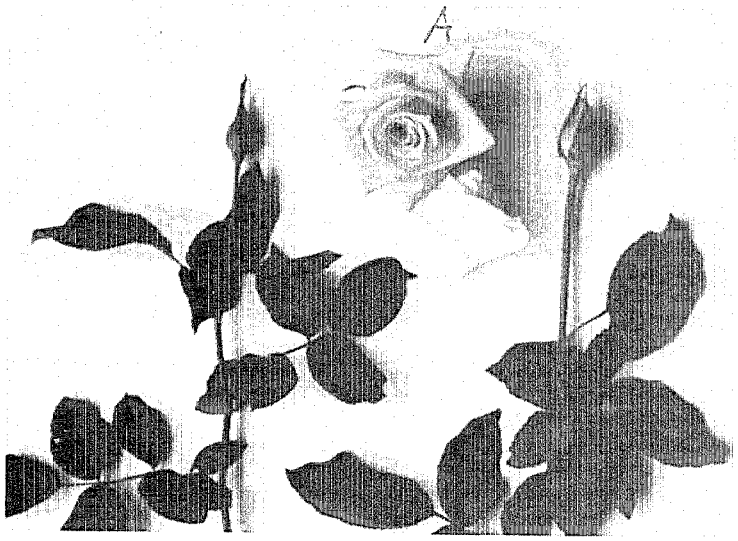
FIG. 1 shows buds in varying stages of opening as well as foliage and flowering stems.
Figure 2:
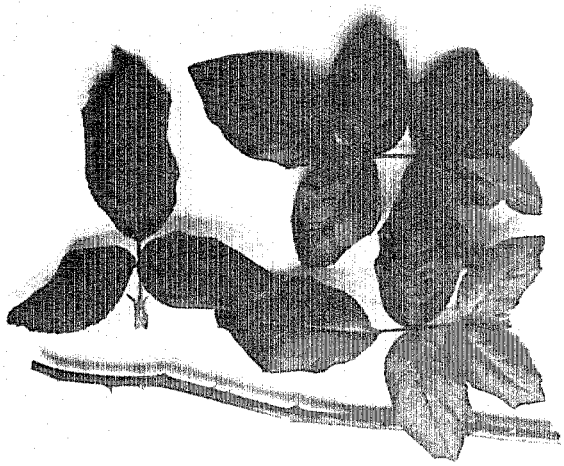
FIG. 2 shows foliage and a stem in greater detail.
Figure 3:
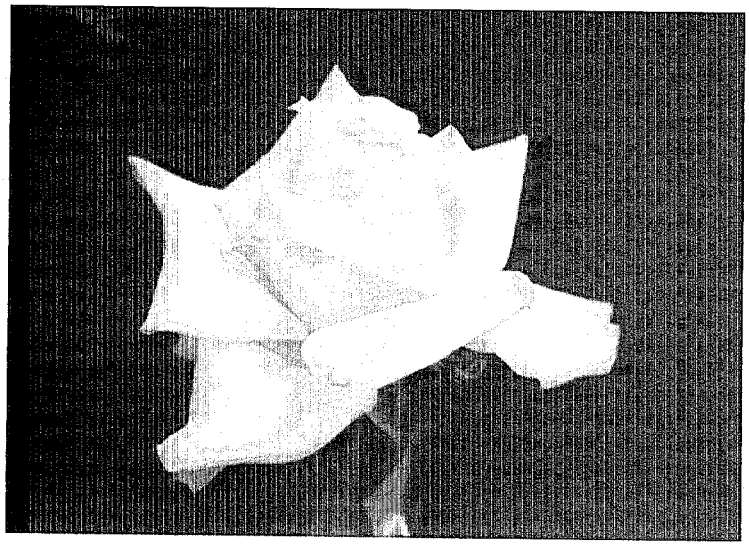
FIG. 3 shows a flower about 25–33% open.
Figure 4:
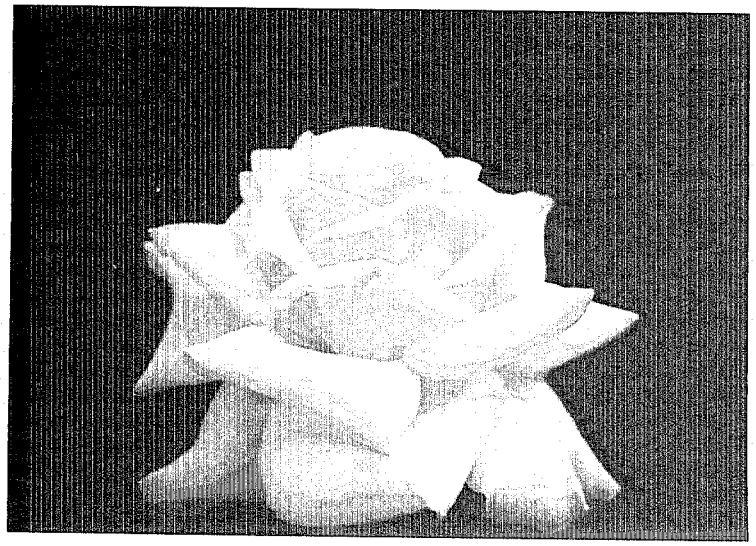
FIG. 4 shows a flower about 80–85% open.

The following is a detailed description of my new rose cultivar with color terminology in accordance with the Royal Horticultural Society (London) Color Chart, except where ordinary dictionary significance of color is indicated.

Parentage:

*Seed parent.*—Peggy Lee.

*Pollen parent.*—Captain Henry Stebbings.

Classification:

*Botanical.*—*Rosa hybrida.*

*Commercial.*—Hybrid tea.

FLOWER

Observations made from specimens grown in outdoor environment in areas surrounding Hilo, Hawaii, in 1994.

Blooming habit: Recurrent, around 36 to 42 days.

Bud:

*Size.*—About 1¾ inches long when the petals begin to unfurl.

*Form.*—Long, pointed, ovoid.

*Color.*—When sepals first divide, the bud is a medium pink shade, Red Group 52D. At the one-fourth open stage, the outside (reverse) of the petals remains the same, but the upper sides are beginning to become a lighter pink shade, Red Group 51D.

*Sepals.*—Color: Green Group 132B; normally 5. Surface texture: Smooth.

*Receptacle.*—Color: Green Group 139C. Shape: Narrow funnel. Size: Small. Surface: Smooth.

*Peduncle.*—Length: 4 to 4½ inches. Surface: Occasional short dull prickles, dark green. Color: Similar to Green Group 137A. Strength: Stiff, erect.

Bloom:

*Size.*—Large. Average open diameter is 5½ to 6 inches.

*Borne.*—Singly.

*Stems.*—Long, 22 to 26 inches on average.

*Form.*—High center; after 3 or so days, center loosens, outer petals curl back.

*Petalage.*—Normally aroung 60, occasionally up to 66.

*Color.*—The reverse sides of the petals begin as a medium pink shade, Red Group 52D, which lightens to Red Group 55C. At the one-fourth open stage, the upper sides begin to become a lighter pink shade, Red Group 51D. When ½ open, the upper surface of the petals become a very light pink, Red Group 56D. As the bloom opens further, this light pink gradually takes on a bright sheen and this light pink sheen lasts until the bloom begins to disintegrate.

*Variegations.*—Occasional white streak on guard petals. In San Diego, Calif., climate, this streak and the guard petals can have a light green cast.

*Discoloration.*—No general tonality change after reaching the ¾- to full-open stage, until flower is almost ready to disintegrate.

*Fragrance.*—Moderately strong, sweet.

Petals:

*Texture.*—Thick (Very resistant to rain damage.)

*Shape.*—Round to deltoid.

*Form.*—Recurved.

*Arrangement.*—Imbricated.

*Persistence.*—Petals drop after 6 to 7 days.

*Lastingness.*—On plant, 6 to 7 days. As a cut flower, about 8 to 10 days.

Reproductive parts:

*Anthers.*—Size: Medium. Quantity: Moderate number. Color: Medium yellow. Arrangement: Regular around styles.

*Filaments.*—Color: Pink.

*Pollen.*—Color: Light orange.

*Styles.*—Color: Light green.

*Stigmas.*—Color: Orange pink.

Plant:

*Form.*—Bush.

*Growth.*—Very vigorous, upright, branching. The plant grows to be medium to medium tall in height, and will reach six to six and one-half feet.

Foliage:

*Number of leaflets on normal, mid-stem leaves.*—5 or 7.

*Size.*—Large, mature leaf is 5½ to 6 inches long.

Quantity.—Abundant.

*Color.*—New foliage is dark green, glossy and maintains same coloration indefinitely.

Leaflets:

*Shape.*—Pointed oval.

*Texture.*—Leathery, glossy.

*Edge.*—Serrated.

*Serration.*—Medium.

*Petiole rachis.*—Color: Green.

*Petiole underside.*—Smooth.

*Stipules.*—Medium, about ½ inch long, bearded.

*Disease resistance.*—Very resistant to black spot and mildew under normal outdoor growing conditions in the East Hawaii area of the Big Island.

Wood:

*New wood.*—Color: Green. Bark: Smooth.

*Old wood.*—Color: Green. Bark: Smooth.

Prickles:

*Quantity.*—Ordinary quantity on main canes from base and on laterals from main canes.

*Form.*—Medium to short, about ¼ inch long, hooked slightly down.

*Color when young.*—Green.

Small prickles:

*Quantity.*—A few on lower stems and laterals.

I claim:

1. The new and distinct cultivar of hybrid tea rose plant, substantially as herein shown and described, characterized particularly as to novelty by the unique coloration of its blooms and also the long durability of its blooms; and combined with these qualities, the long cutting stems and attractive foliage plus quite good fragrance.

* * * * *